United States Patent
Adams et al.

(10) Patent No.: US 6,602,271 B2
(45) Date of Patent: Aug. 5, 2003

(54) COLLAPSIBLE BLOOD FILTER WITH OPTIMAL BRAID GEOMETRY

(75) Inventors: Bruce Adams, Malden, MA (US); Ahmed Malek, Cairo (EG); Jerry R. Brightbill, Newton, MA (US); Nasser Rafiee, Andover, MA (US); Nareak Douk, Lowell, MA (US); David S. Brin, Danvers, MA (US); Dennis L. Brooks, Windsor, CA (US); Robert D. Lashinski, Sebastopol, CA (US)

(73) Assignee: Medtronic Ave, Inc., Santa Rosa, CA (US)

( * ) Notice: Subject to any disclaimer, the term of this patent is extended or adjusted under 35 U.S.C. 154(b) by 231 days.

(21) Appl. No.: 09/735,140

(22) Filed: Dec. 12, 2000

(65) Prior Publication Data

US 2002/0004667 A1 Jan. 10, 2002

Related U.S. Application Data (63) Continuation-in-part of application No. 09/578,244, filed on May 24, 2000.

(51) Int. Cl.⁷ .............................................. A61M 29/00
(52) U.S. Cl. ....................................... 606/200; 606/191
(58) Field of Search ................................ 606/200, 191, 606/194, 195, 198, 199

(56) References Cited

U.S. PATENT DOCUMENTS

| | | |
|---|---|---|
| 4,425,908 A | 1/1984 | Simon |
| 4,723,549 A | 2/1988 | Wholey et al. |
| 4,790,812 A | 12/1988 | Hawkins, Jr. et al. |
| 4,873,978 A | 10/1989 | Ginsburg |
| 4,926,858 A | 5/1990 | Gifford, III et al. |
| 5,071,407 A | 12/1991 | Termin et al. |
| 5,108,419 A | 4/1992 | Reger et al. |

(List continued on next page.)

FOREIGN PATENT DOCUMENTS

| | | | |
|---|---|---|---|
| WO | 96/01591 A1 | 1/1996 | |
| WO | 98/33443 A1 | 8/1998 | |
| WO | 99/16382 A2 | 4/1999 | |
| WO | 99/22673 A1 | 5/1999 | |
| WO | 99/23976 A1 | 5/1999 | |
| WO | WO/99/23976 * | 5/1999 | .................. 606/200 |
| WO | 00/44308 A2 | 8/2000 | |
| WO | 01/05329 A1 | 1/2001 | |
| WO | 01/08595 A1 | 2/2001 | |
| WO | 01/15929 A1 | 3/2001 | |
| WO | 01/21100 A1 | 3/2001 | |
| WO | 02/05729 A2 | 1/2002 | |

*Primary Examiner*—Gloria M. Hale
(74) *Attorney, Agent, or Firm*—Medtronic Ave, Inc.

(57) ABSTRACT

The present invention is a collapsible blood filter for use during a vascular procedure, such as angioplasty or stent deployment. A filter made of braided filaments is located on the distal end of a delivery member, and the filter is deployed downstream of the vascular treatment site to capture emboli released during and immediately after the procedure. Optimal braid geometry of the filter ensures that captured emboli will be retained during collapse and removal of the filter following the procedure.

18 Claims, 6 Drawing Sheets

U.S. PATENT DOCUMENTS

| | | | |
|---|---|---|---|
| 5,160,342 | A | 11/1992 | Reger et al. |
| 5,329,942 | A | 7/1994 | Gunther et al. |
| 5,421,832 | A | 6/1995 | Lefebvre |
| 5,527,282 | A | 6/1996 | Segal |
| 5,549,626 | A | 8/1996 | Miller et al. |
| 5,695,519 | A | 12/1997 | Summers et al. |
| 5,769,816 | A | 6/1998 | Barbut et al. |
| 5,814,064 | A | 9/1998 | Daniel et al. |
| 5,827,324 | A | 10/1998 | Cassell et al. |
| 5,888,201 | A | 3/1999 | Stinson et al. |
| 5,910,154 | A | 6/1999 | Tsugita et al. |
| 5,935,139 | A | 8/1999 | Bates |
| 5,941,869 | A | 8/1999 | Patterson et al. |
| 5,941,896 | A | 8/1999 | Kerr |
| 5,972,019 | A | 10/1999 | Engelson et al. |
| 6,059,814 | A | 5/2000 | Ladd |
| 6,063,113 | A | 5/2000 | Kavteladze |
| 6,066,149 | A | 5/2000 | Samson et al. |
| 6,066,158 | A | 5/2000 | Engelson et al. |
| 6,096,053 | A | 8/2000 | Bates |
| 6,123,715 | A | 9/2000 | Amplatz |
| 6,136,016 | A | 10/2000 | Barbut et al. |
| 6,152,946 | A | 11/2000 | Broome et al. |
| 6,165,200 | A | 12/2000 | Tsugita et al. |
| 6,171,327 | B1 | 1/2001 | Daniel et al. |
| 6,346,116 | B1 * | 2/2002 | Brooks et al. ............... 606/200 |

* cited by examiner

COLLAPSIBLE BLOOD FILTER WITH OPTIMAL BRAID GEOMETRY

This application is a continuation-in-part of U.S. patent application Ser. No. 09/578,244 entitled "Distal Protection Device" and filed May 24, 2000, the contents of which are hereby incorporated by reference.

FIELD OF THE INVENTION

The present invention relates generally to endovascular devices for capturing particulate. More particularly, the invention relates to a filter assembly located at the distal end of a delivery member to capture emboli in a blood vessel during a vascular procedure and then remove the captured emboli from the patient after completion of the procedure.

BACKGROUND OF THE INVENTION

A variety of treatments exists for dilating or removing athersclerotic plaque in blood vessels. The use of an angioplasty balloon catheter is common in the art as a minimally invasive treatment to enlarge a stenotic or diseased blood vessel. This treatment is known as percutaneous transluminal angioplasty, or PTA. To provide radial support to the treated vessel in order to prolong the positive effects of PTA, a stent may be implanted in conjunction with the procedure.

Thrombectomy is a minimally invasive technique for removal of an entire thrombosis or a sufficient portion of the thrombosis to enlarge the stenotic or diseased blood vessel may be accomplished instead of a PTA procedure. Atherectomy is another well known minimally invasive procedure that mechanically cuts or abrades a stenosis within the diseased portion of the vessel. Alternatively, ablation therapies use laser or RF signals to superheat or vaporize the thrombis within the vessel. Emboli loosened during such procedures may be removed from the patient through the catheter.

During each of these procedures, there is a risk that emboli dislodged by the procedure will migrate through the circulatory system and cause clots or strokes. Thus, practitioners have approached prevention of escaped emboli through use of occlusion devices, filters, lysing and aspiration techniques. In atherectomy procedures, it is common to remove the cut or abraded material by suction though an aspiration lumen in the catheter or by capturing emboli in a filter or occlusion device positioned distal of the treatment area.

Prior art temporary filters or occlusion devices are associated with either a catheter or guidewire and are positioned distal of the area to be treated. One prior art collapsible filter device includes a filter deployed by a balloon distal of a dilatation balloon on the distal end of a catheter. The filter consists of a filter material secured to resilient ribs. The ribs are mounted at the distal end of the catheter. A filter balloon is located between the catheter exterior and the ribs. Inflation of the filter balloon extends the ribs outward across the vessel to form a trap for fragments loosened by the dilatation balloon. When the filter balloon is deflated, the resilient ribs retract against the catheter to retain the fragments during withdrawal of the catheter.

Another prior art filter arrangement includes several filter elements fastened in spaced apart arrangement along the length of a flexible elongate member. This forms an open-mouthed tubular sock-like arrangement to capture the emboli within. The filter is collapsed around the flexible elongate member by wrapping it spirally.

Yet another prior art filter includes a filter mounted on the distal portion of a hollow guidewire or tube. A core wire is used to open and close the filter. The filter has an expandable rim at its proximal end formed by the core wire. The filter is secured at the distal end to the guide wire.

Another prior art device has a filter made from a shape memory material. The device is deployed by moving the proximal end of the filter towards the distal end. It is collapsed and withdrawn by sliding a sheath over the filter and then removing the sheath and filter together.

A further prior art filter device discloses a compressible polymeric foam filter mounted on a shaft that is inserted over a guidewire. The filter is inserted collapsed within a housing which is removed to deploy the filter once in position. The filter is retracted by inserting a large bore catheter over the shaft and the filter, and then removing the shaft, filter and catheter together.

Another prior art filter arrangement has a filter comprised of a distal filter material secured to a proximal framework. This filter is deployed in an umbrella manner with a proximal member sliding along the shaft distally to open the filter and proximally to retract the filter. A large separate filter sheath can be inserted onto the shaft and the filter is withdrawn into the sheath for removal from the patient.

Other known prior art filters are secured to the distal end of a guidewire with a tubular shaft. Stoppers are placed on the guidewire proximal and distal of the filter, allowing the filter to move axially and retract independently of the guidewire. A sheath is used to deploy and compress the filter.

A problem associated with known temporary filter arrangements is that emboli may not be fully contained within the filter. Emboli can build up in the area just proximal of the filter, including any frame portion proximal of the filter assembly. As the filter is closed, emboli not fully contained in the filter can escape around the filter into the circulatory system and cause potentially life threatening strokes.

Another known prior art collapsible filter is formed from braided filaments. The pores thus created change in size and shape as the filter expands during deployment or as the filter collapses for removal. However, there are previously unrecognized problems associated with the changing of pore sizes during use of a braided filter. Depending on the braid geometry of the filter, the pore size may increase during the transition of the filter from the expanded, or deployed size to a smaller size required for removal of the filter from the body. This problem is critical during retrieval of the filter when an increase in pore size may allow the escape of embolic material previously captured by the filter.

Therefore, what is needed is a filter arrangement that addresses the problem of emboli not fully contained in the filter assembly. Furthermore, there is a need for a filter assembly that is adaptable for delivery with standard PTCA balloon or stent delivery catheters. Additionally there is a need for a filter arrangement that is secure by being mounted at its distal and proximal ends to the delivery member ensuring proper placement of the filter throughout deployment, capture of the emboli and subsequent removal of the filter and captured emboli. There is also a need for a braided filter with optimal braid geometry to ensure that the pores of the filter do not become larger during removal, when the filter transitions between a deployed size and a collapsed size.

SUMMARY OF THE INVENTION

The present invention is a distal protection device for use in vascular procedures. The distal protection device includes a filter assembly adjacent the distal end of a delivery member used in the procedure. The proximal and distal ends of the filter assembly are fixed to the delivery member such that the ends cannot move longitudinally along the delivery member, but may rotate independently of the delivery member core. The filter assembly includes an expandible frame with a distal portion acting as the emboli filter. The emboli filter is sized sufficiently to expand and cover the cross sectional area of the vessel distal of the intended treatment area.

The filter assembly may have a variety of configurations. In one embodiment, the frame consists only of the proximal portion of the filter assembly, with the distal half formed from filter material. The frame can have a braided configuration or consist of a sinusoidal ring element adjacent the filter material with helical segments extending from the sinusoidal ring to the delivery member. In another embodiment, the frame forms a basket arrangement and includes the filter material in the distal half of the basket. Such a frame can be configured with a tighter braid on the distal end, thus obviating the need for a separate filter material. This embodiment may have a generally ovoid shape.

The filter assembly further includes a moveable sheath for positioning the emboli filter between an expanded position and a collapsed position. The sheath extends over the frame, collapsing the frame and filter of the assembly as they are drawn into the sheath. Likewise, when the frame and filter are removed from the sheath, they will expand so that the filter will cover the cross sectional area of the vessel distal of the treatment area.

Alternative embodiments of the filter assembly can include an aspiration lumen and/or a flushing lumen extending through the sheath. This allows large emboli to be lysed or aspirated prior to retracting the filter and removing it from the patient.

Another alternative embodiment of the filter assembly has the proximal end of the filter longitudinally fixed to the delivery member, the distal end of the filter being slidingly attached to the member. When a sheath is passed over the filter to compress it for delivery or retrieval, the distal end of the filter slides distally on the delivery member, extending the length of the filter. The filter of this embodiment may also include a frame that is densely braided to form a basket with fine pores. The filter also has large inlet openings that are formed in the proximal end. The deployed shape of this filter embodiment is generally that of a teardrop, the proximal end having a generally obtuse cone and the distal end having a generally acute cone. A cylindrical well defines the filter body between the proximal and distal cones.

For embodiments that utilize tightly braided frame elements to form the filter medium, the braid geometry is optimized such that the pores only get smaller in size as the filter is collapsed for retraction. In this way, emboli that have been trapped in the braided filter during an endovascular procedure will not escape through the filter orifices as they change shape during the filter withdrawal procedure.

The sheath is configured to be used with either a rapid exchange arrangement or an over-the-wire arrangement as is well known to those skilled in the art.

The figures are not necessarily to scale.

DETAILED DESCRIPTION OF THE PREFERRED EMBODIMENTS

Figure 1:
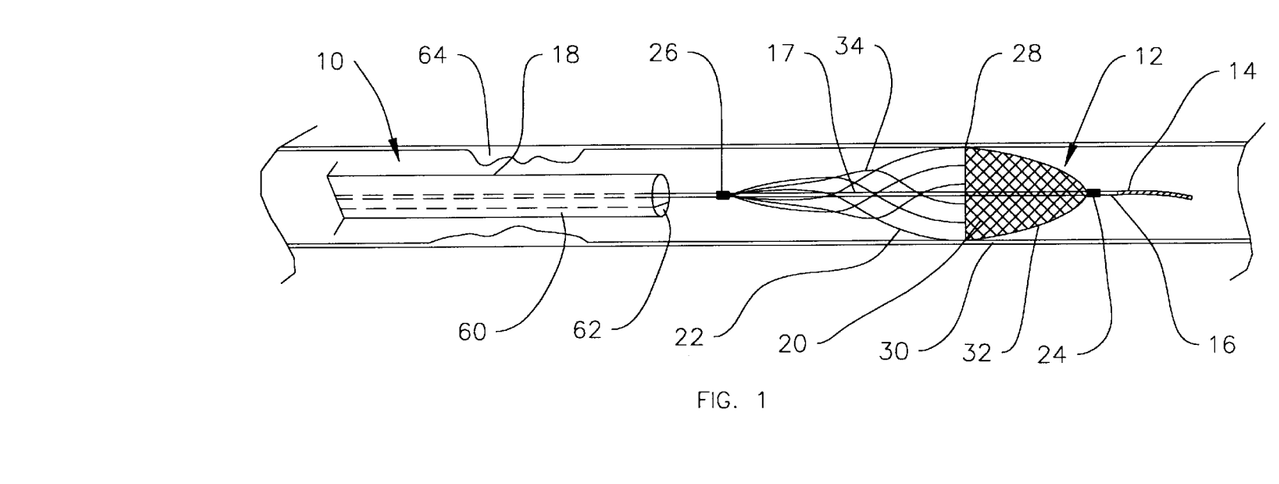
FIG. 1 is a side view of a catheter and delivery member incorporating a distal protection device of the present invention, with the distal protection device shown deployed in a vessel.
Figure 2:
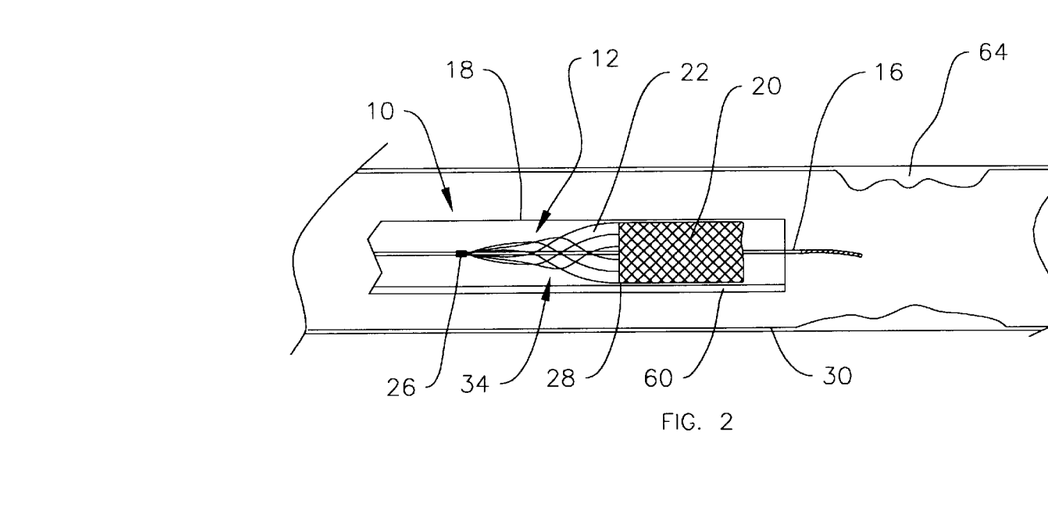
FIG. 2 is a side view taken of the distal portion of a catheter and delivery member incorporating a distal protection device of the present invention, with the distal protection device shown constrained in the catheter, which is shown in section.

The present invention is a distal protection device, designated 10 in FIG. 1 for use in minimally invasive procedures, such as vascular procedures or other procedures where the practitioner desires to capture material that may be dislodged during the procedure. Distal protection device 10 includes filter assembly 12 located adjacent distal end 14 of delivery member 16. In this preferred embodiment delivery member 16 can be a modified guidewire assembly, hereinafter referred to as either "delivery member," "guidewire," or "core wire." Filter assembly 12 is delivered, deployed and retrieved by sheath 18, which is slidable over filter assembly 12. When distal protection device 10 is in a constrained position, filter assembly 12 is collapsed within sheath 18 as shown in FIG. 2. When filter assembly 12 is deployed, sheath 18 is withdrawn, releasing filter assembly 12 as shown in FIG. 1.

Filter assembly 12 includes filter 20 and frame 22 and is secured to delivery member 16 at distal filter portion 24 and proximal filter portion 26. Preferably, filter assembly ends 24 and 26 are fixed in the longitudinal position, but are capable of rotational movement independent of guidewire core 17 while maintaining the longitudinal position. Filter 20 is formed from a suitable mesh or porous material that will filter emboli from blood while permitting sufficient perfusion therethrough. For example, a porous filter can be formed from urethane material by adding salt, sugar or other granular particles during the casting of the urethane filter. Following the cutting and curing processes, these granular particles are dissolved forming a porous urethane filter as is well known to those skilled in the art. Other suitable filter materials may include ePTFE or other Teflon® fluoropolymers by DuPont de Nemours in Wilmington, Del., Kevlar® para-aramid, also by DuPont, or nylon and the like having an appropriate porous construction to filter emboli from blood passing through the filter.

Filter assembly 12 is positioned concentric with delivery member 16. Filter 20 is sized such that when it is fully deployed, as in FIG. 1, filter proximal edge 28 will contact the inner surface of blood vessel wall 30. The surface contact is preferably maintained over the entire cross section to prevent any emboli from escaping past filter 20. Filter 20 is preferably secured at proximal filter edge 28 to frame 22 and at distal filter portion 32 to the delivery member 16.

Frame 22 of filter assembly 12 is an expandable frame made from a shape memory material such as nitinol, stainless steel, a suitable polymer or other suitable materials. Several struts, designated generally as 34, extend from a connection with delivery member 16 at proximal filter portion 26 to proximal edge 28 of filter 20, to form frame 22, as seen in FIGS. 1 and 2.

Figure 3:
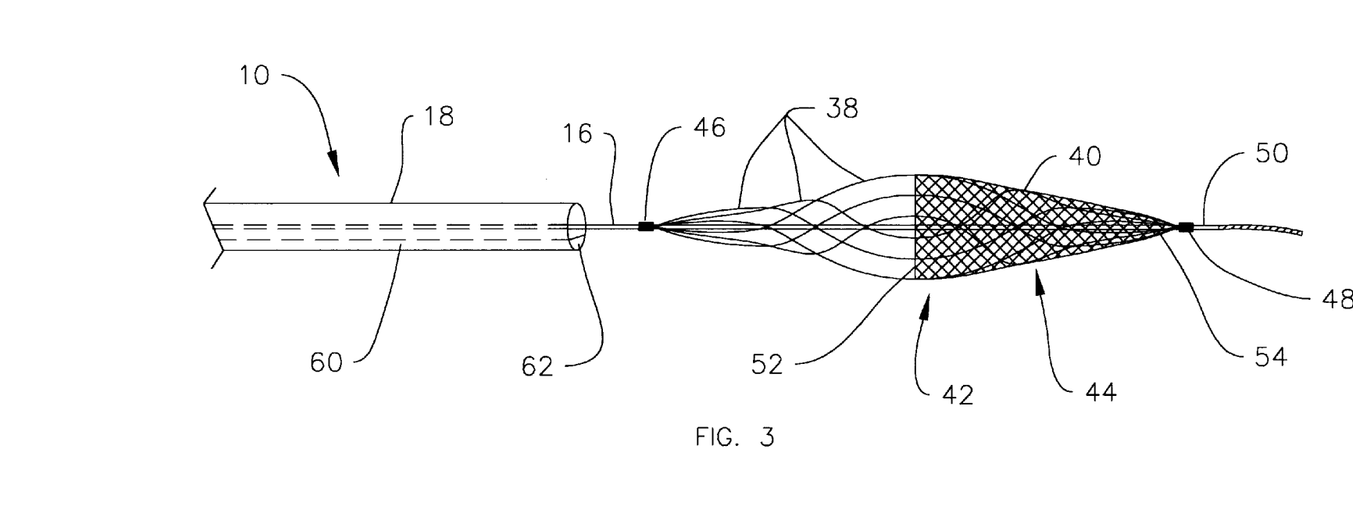
FIG. 3 is a side view of a second filter arrangement of the present invention, shown deployed.

Alternatively, struts 38 may extend around filter 40 forming basket frame 42 with filter 40 on at least distal portion 44 of basket frame 42 as shown in FIG. 3. In such an arrangement, basket frame 42 is secured preferably at proximal and distal ends 46, 48 respectively to guidewire 50. As with the embodiment of FIG. 1, basket frame 42 is fixed on the guidewire at a longitudinal position where it is capable of rotational movement independent of guidewire 50. Filter 40 is secured at its proximal and distal ends 52, 54 to basket frame 42. Filter 40 can be secured to struts 38 on the distal portion 44 of basket frame 42. Alternatively, filter 40 may be formed on basket frame 42 by dip coating select portions of basket frame 42 with a suitable material such as urethane and treating the material to form the desired porous structure on distal portion 44.

A variety of strut configurations are suitable including the braid configuration shown in FIG. 1. Struts 56 of filter assembly basket 58 shown in FIG. 4 have a dense braid on distal portion 61 that transitions to a less dense braid on proximal portion 63. Filter material may be located on distal portion 61 either by having a separate filter material or by dip coating selected portions of the basket 58 as discussed above with respect to the embodiment shown in FIG. 3. Alternatively, struts 56 may act as braid filaments, the braid being sufficiently dense on distal portion 61 to act as a filter, thus obviating the need for separate filter material or selective dip coating of basket 58. As mentioned with respect to expandable frame 22 in FIG. 1, braid filaments may be made of shape-memory metal, such as nitinol, stainless steel, or of non-metallic materials that are sufficiently resilient to provide a self-supporting filter assembly. To enhance visualization of the braided filter under fluoroscopy, at least one of the filaments may be a wire that is made of, or plated with, a radiopaque metal such as gold, platinum, tungsten or alloys thereof. Filter assembly basket 58 is fixed to the guidewire 65 at its proximal and distal filter ends 66, 68. Again, filter assembly basket 58 is preferably fixed at a longitudinal position on guidewire 65 where it is capable of rotational movement independent of the guidewire core. Sheath 70 is used to deploy filter assembly basket 58.

Figure 5:
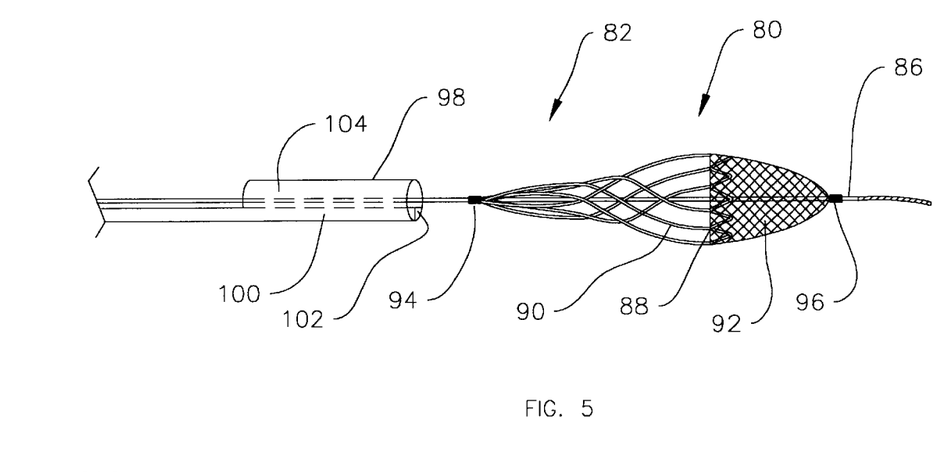
FIG. 5 is a side view of a rapid exchange styled delivery sheath and a fourth filter arrangement of the present invention.

Filter assembly 80 shown in FIG. 5 is similar to the filter arrangement of FIG. 1. Frame 82 consists of distal ring 84 formed from a sinusoidal element. Extending from ring 84 to guide wire 86 are helical members 90. For example, one such member 90 extends between apex 88 of ring 84 and guidewire 86. Distal end 96 of filter 92 is secured to guidewire 86.

Sheath 98 includes aspiration lumen 100 and lysing lumen 102. While two lumens are shown, as known to those skilled in the art, either lumen 100 or lumen 102 alone may be incorporated in sheath 98. Sheath 98 also includes a short guidewire lumen 104 providing a sheath configured as a rapid exchange sheath.

Figure 6:
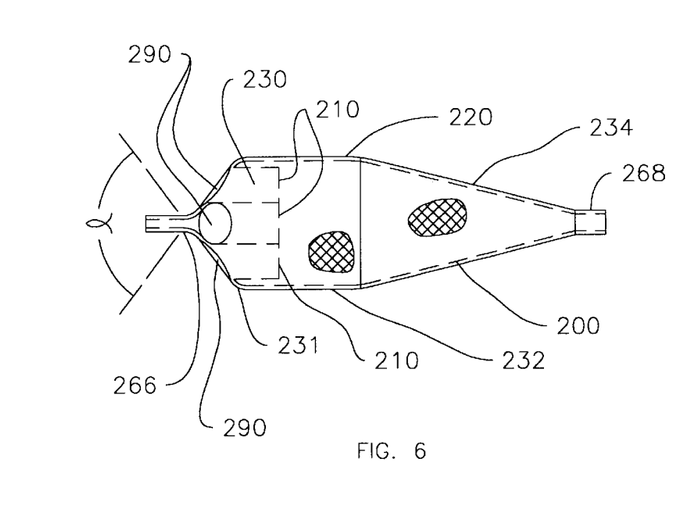
FIG. 6 is a side view of a fifth filter arrangement of the present invention.

FIG. 6 shows a fifth filter arrangement surrounding a body forming mandrel. This filter embodiment may be used in the previously described filter assemblies, especially that of FIG. 4. Filter 220 is shaped to have cylindrical central well 232, distal cone 234, proximal surface 230, and proximal and distal ends 266 and 268, respectively. Either sheath 18 or sheath 98 can be used to transform filter 220 between its generally teardrop shaped, deployed configuration shown in FIG. 6 and a collapsed configuration similar to that of filter assembly 12, shown in FIG. 2.

Figure 7:
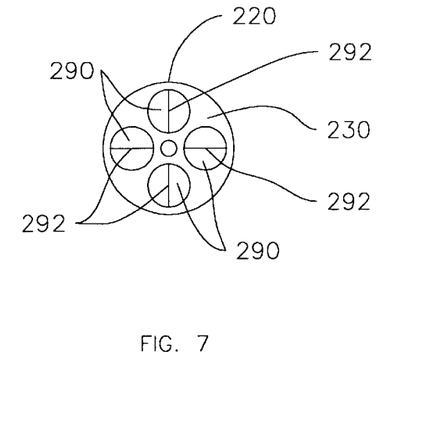
FIG. 7 is view of the inlet end of the fifth filter arrangement shown in FIG. 6.

The cylindrical shape of central well 232 provides greater surface area for contacting the vessel wall. With greater contact area, filter 220 will have more secure apposition against the vessel wall during treatment. Cylindrical well 232 can also provide a larger inner volume for collection of emboli. Rounded shoulder 231 forms the transition from surface 230 to cylindrical central well 232. As viewed from the proximal end, four inlet ports 290 are equally spaced around proximal surface 230, each port having an axis 292 in-plane with a radius of the central well 232. The included cone angle α of proximal surface 230 is preferably more than 90°, most preferably about 100°. The combination of cone angle α and rounded shoulder 231 has shown a reduced likelihood of scraping the vessel wall and an improved particulate collection efficiency.

Figure 4:
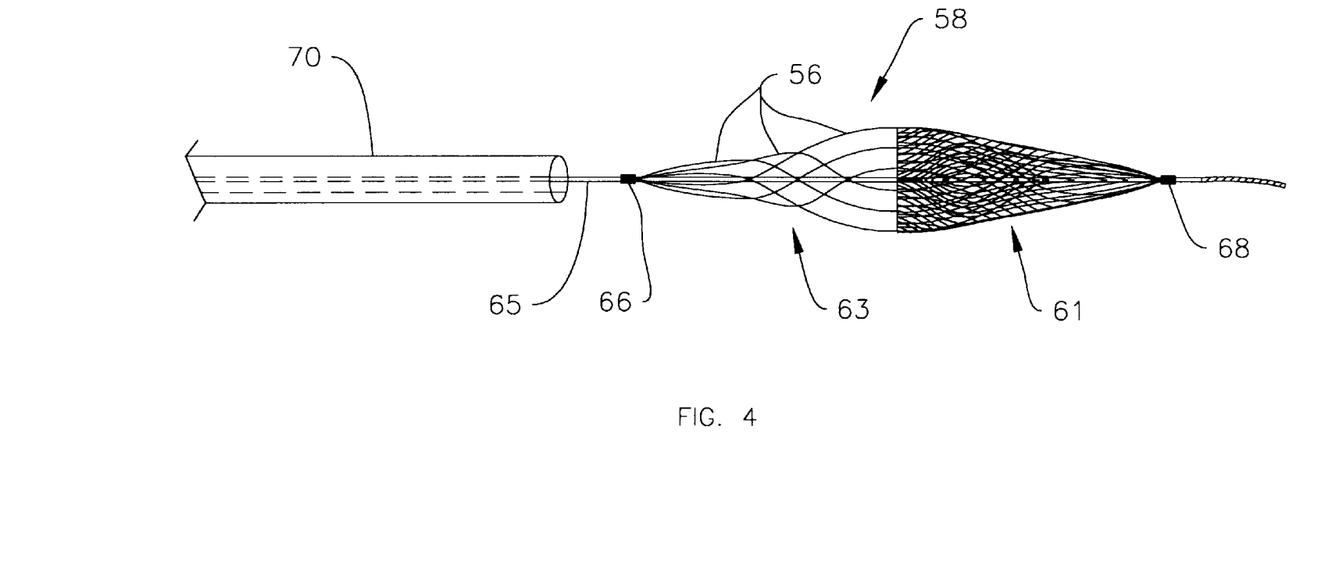
FIG. 4 is a side view of a third filter arrangement of the present invention, shown deployed.
Figure 10:
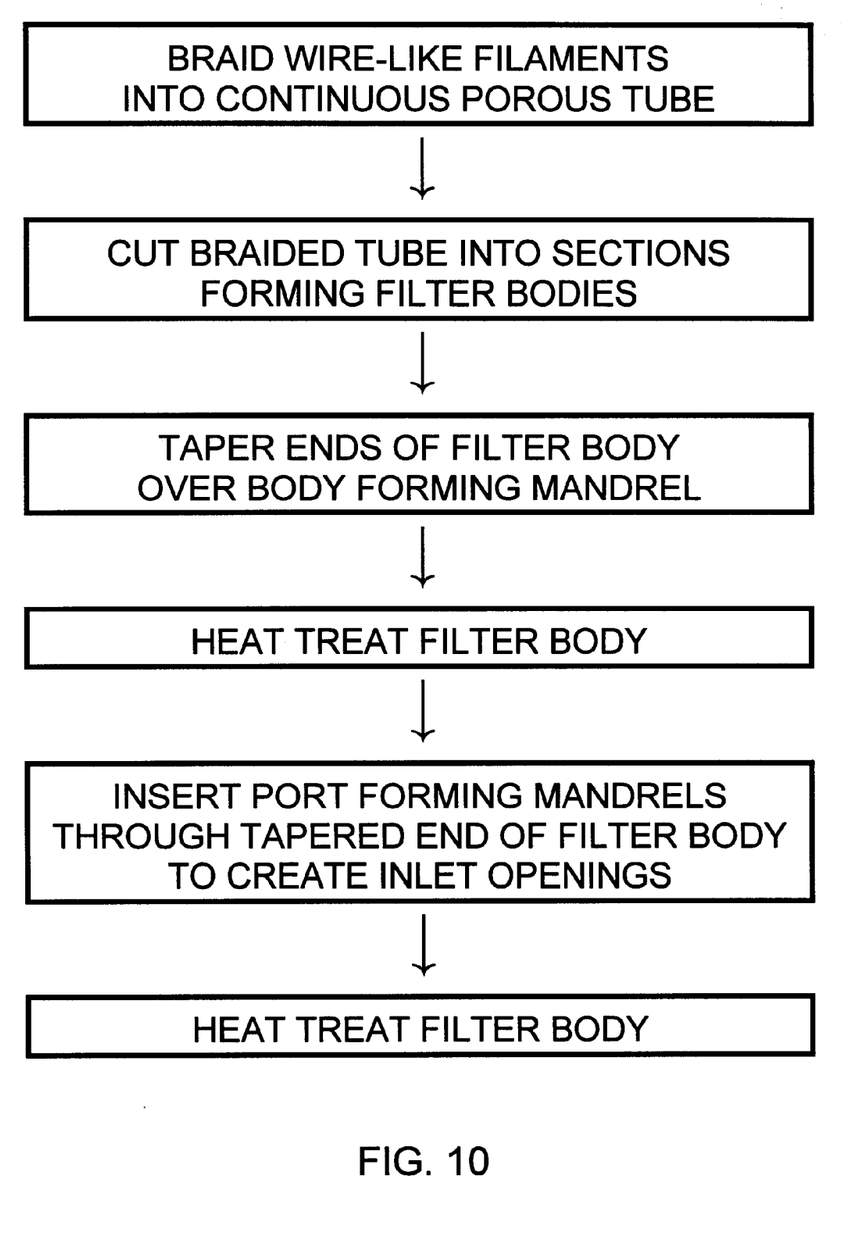
FIG. 10 is a flow chart depicting the method of making the fifth filter arrangement shown in FIG. 6.

Filter 220 is similar to filter assembly basket 58 shown in FIG. 4, wherein the struts 56 alone make the filter basket by using a densely braided structure. Filter 220 is formed with a generally constant pitch braid, preferably providing a uniform pore size of approximately 75–125 microns, such that no additional filter material is necessary. As depicted schematically in FIG. 10, filter 220 is made from a continuous braided tube, which is cut into sections to form individual filter bodies. Filter 220 is tapered at the ends, preferably by drawing filter ends 266, 268 over body forming mandrel 200. While filter ends 266, 268 are held in position, filter 220 is heat treated at a time and temperature suitable for the selected braid filament material, as is well known to those of skill in the art. Inlet ports, or openings 290 are formed by inserting port forming mandrels, not shown, through pores in surface 230 and into mandrel retaining holes 210 in body forming mandrel 200. Preferably, a second heat treatment is applied to the braid of filter 220, after which all mandrels are removed and filter 220 recovers to its heat set shape. Optionally, a single heat treatment can be used to form both filter 220 and ports 290.

Ports 290 are best described when viewed from the proximal end of the filter 220 because this view shows the shapes of the mandrels used to make inlet ports 290. Ports 290 provide filter inlet openings that are substantially larger than the size of the pores in filter 220. Ports 290 may have a variety of preferably rounded, symmetrical shapes, each having an axis 292 in-plane with a radius of the cylindrical central well 232. To efficiently gather particulate matter, ports 290 should also expose as much of the proximal surface 230 as possible, especially near its perimeter, without compromising the structural integrity of filter 220. Such ports 290 will have axes 292 as long as possible, such as approximately 90% of the difference between the radius of central well 232 and the radius of proximal end 266.

Figure 8A:
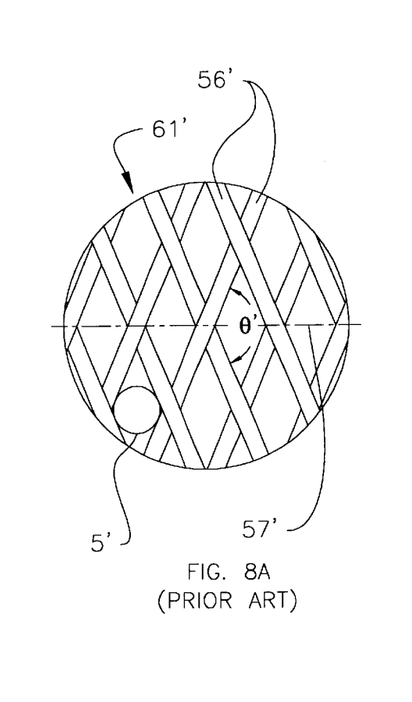
FIG. 8A is an enlarged view of a section of braid material utilized in a blood filter of the prior art.
Figure 8B:
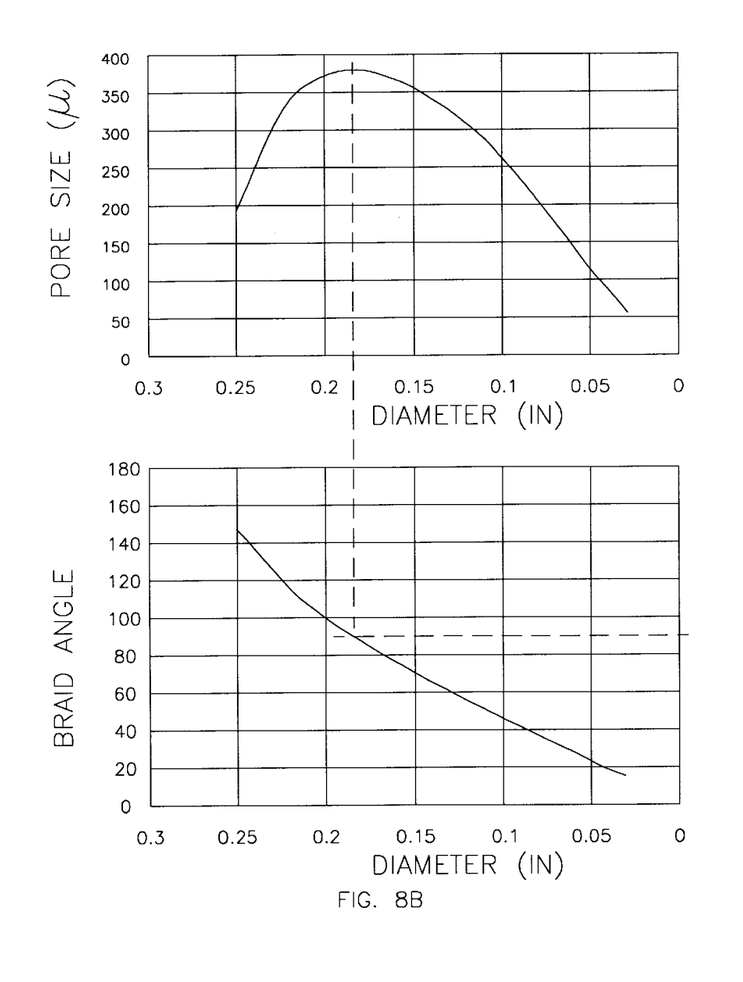
FIG. 8B shows two graphs depicting corresponding changes in pore size and braid angle as the prior art braid of FIG. 8A changes in diameter.

FIG. 8A shows a section of braided distal portion 61' of prior art blood filters and FIG. 8B shows the concomitant problem solved by the current invention. In FIG. 8A, braid filaments 56' form a fully deployed tubular filter body having axis 57'. Braid angle θ' is formed between braid filaments 56', and is measured across axis 57'. Pore size 5' depicts the size of a spherical particle that can pass through the orifices formed in braided distal portion 61'. In braided tubular structures, such as filters, changes in diameter are accompanied not only by changes in length, but more importantly by changes in the dimensions of the rhombus-shaped orifices formed between braid filaments. For example, lengthening the tubular filter will cause lengthening of the orifice in the direction parallel to the axis of the body, and synchronous shortening of the orifice in the circumferential direction. When such lengthening begins, if the orifice is shorter in the axial direction than in the circumferential direction, then the cross-sectional area, and especially the pore size of the orifice will increase until the orifice becomes square. In the prior art embodiment of FIG. 8A, angle θ' is greater than a critical angle of 90°, such that pore size 5' will actually increase during collapse of the filter until the filter diameter reaches a point where angle θ' passes through the critical angle. Emboli that have been trapped in the braided filter during an endovascular procedure may escape through the filter orifices as these filter orifices grow in size during collapse and withdrawal of the filter. After the orifices reach a maximum size, when angle θ' is at the critical angle, the orifices will begin shrinking as the filter continues to collapse. FIG. 8B shows this undesirable change in pore size in prior art Example 1 which has the following properties.

| Example 1 | |
|---|---|
| Wire thickness | 0.002 in. |
| Pics/in. | 100 |
| Number of wire carriers | 48 |
| Braid diameter | 0.25 in |
| Braid angle, across axis | 146° |

In accordance with the invention, the optimal braid geometry for collapsible blood filters has been found to include an inter filament braid angle of not more than 90°, as measured across the axis. Example 2 is a collapsible blood filter having this optimal geometry and having been braided in conformance with the following parameters.

Figure 9A:
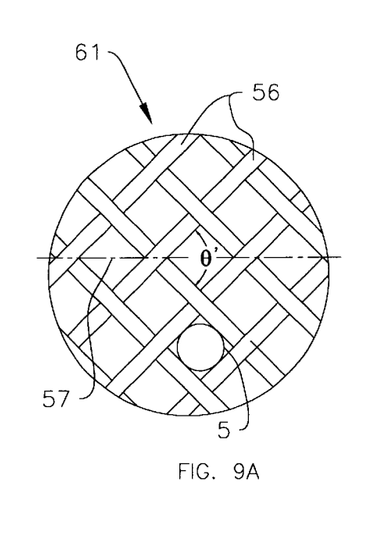
FIG. 9A is an enlarged view of a section of braid material utilized in a blood filter of the present invention.

| Example 2 | |
|---|---|
| Wire thickness | 0.002 in. |
| Pics/in. | 92 |
| Number of wire carriers | 144 |
| Braid diameter | 0.25 in |
| Braid angle, across axis | 90° |

Figure 9B:
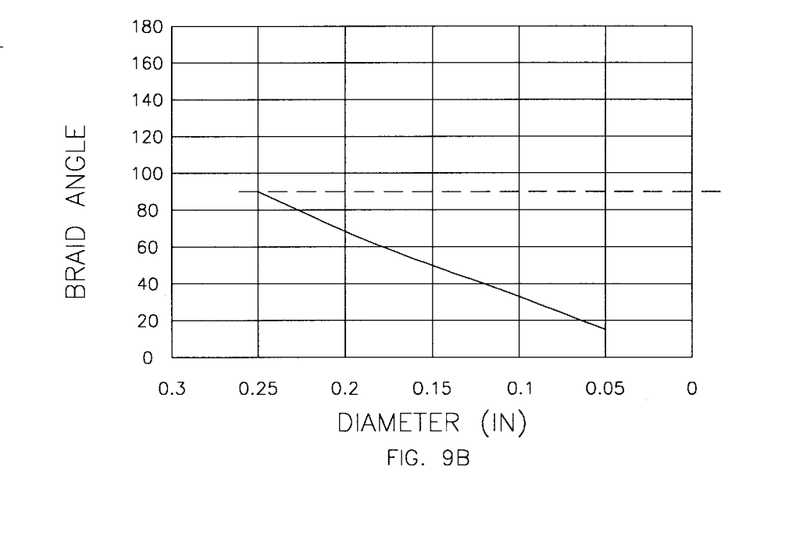
FIG. 9B shows two graphs depicting corresponding changes in pore size and braid angle as the braid of FIG. 9A changes in diameter.

FIG. 9A shows a section of braided distal portion 61 of Example 2. Braid filaments 56 form a fully deployed tubular filter body having axis 57. Braid angle θ is formed between braid filaments 56, and is measured across axis 57. FIG. 9B shows that, as the braid of Example 2 is collapsed in diameter, pore size 5 only becomes smaller, ensuring that any captured embolic material will remain inside the filter during withdrawal of the device from the patient.

The deployment of filter assembly 12 will now be described, although the procedure explained is equally applicable to any of the filter assembly embodiments disclosed herein. The deployment mechanism includes sheath 18 that is sized to travel over delivery member 16 and receive the filter assembly 12 therein as shown in FIG. 2. Sheath 18 may incorporate an aspiration lumen 60. Additionally, sheath 18 may incorporate a flushing lumen 62 (FIG. 1) to enable the practitioner to flush the filter assembly with a lysing agent prior to and during the procedure to remove emboli lodged on the struts. The sheath is constructed for use as either an over-the-wire system shown with sheath 18 in FIG. 1, or a rapid exchange system, shown with sheath 98 in FIG. 5.

In operation, sheath 18 is extended over delivery member 16 until it fully covers filter assembly 12 as shown in FIG. 2. Sheath 18, filter assembly 12 and delivery member 16 are then inserted into the patient and routed to the area to be treated, designated as 64 in FIG. 1. Filter assembly 12 and sheath 18 are positioned past, or downstream of the area 64 to be treated. Sheath 18 is then withdrawn, releasing struts 34 of filter assembly 12. As struts 34 resume their unrestrained position, filter 20 expands to fill the cross sectional area of the vessel. Sheath 18 may then be completely withdrawn from delivery member 16 and then an appropriate second device, such as a treatment catheter, can be routed over delivery member 16 to the treatment area.

During and after the treatment such as, an angioplasty, atherectomy or the like procedure, emboli can be dislodged. The emboli will travel downstream and be captured by filter 20. The treatment catheter is removed after the procedure and sheath 18 is reloaded on delivery member 16 and is advanced to treatment area 64. Prior to collapsing the filter assembly 12, the practitioner can aspirate the area to remove any loose emboli that may not be sufficiently captured in filter 20. For example, emboli may be lodged on struts 34 proximal of filter 20. When filter 20 is collapsed, these uncollected emboli may escape into the blood stream. Thus, the particles should be removed. Furthermore, the practitioner may choose to flush the area with a lysing agent to reduce the size of the emboli within filter 20 or struts 34 prior to removing the filter.

The practitioner then extends sheath 18 over filter assembly 12 compressing filter 20 and the captured emboli within sheath 18. If filter 20 incorporates filter material that has been braided with optimal geometry as described above, then the pores of the filter will only become smaller during compression of filter 20, and no captured embolic material will escape therethrough. Finally, sheath 18, filter assembly 12 and delivery member 16 can be removed from the patient.

The foregoing embodiments and examples are illustrative and are in no way intended to limit the scope of the claims set forth herein. The filter can be mounted onto a delivery member such as a catheter or integrally with a dilatation balloon for advancing across a tight stenosis. The braid designs are shown in one-over-one configuration, but two-over-two or other configurations are also applicable, as is well known to those of skill in the art. These and other alternatives are within the scope of the invention.

We claim:

1. A collapsible blood filter for capturing emboli during an endovascular procedure at a treatment site, the filter comprising a tube formed by braided filaments that define pores, the filter having at least one inlet opening that is substantially larger than the pores, the filter having an axis and tapered ends, wherein relative movement of the ends along the axis accompanies transformation of the filter between a collapsed configuration and a deployed configuration, and wherein the pore-defining filaments of the braided tube form a maximum included angle of about 90 degrees, as measured across the axis when the filter is in the deployed configuration.

2. The blood filter of claim 1 wherein at least a portion of the filter between the ends is cylindrical in shape when the filter is in the deployed configuration.

3. The blood filter of claim 1 wherein the shape of the deployed configuration is ovoid.

4. The blood filter of claim 1 wherein the deployed configuration is sized to fill a selected cross-sectional area distal to the treatment site.

5. The blood filter of claim 1 wherein at least one of the braid filaments is a wire comprising radiopaque metal.

6. A distal protection device for capturing emboli during an endovascular procedure at a treatment site, the device comprising:

a delivery member having a proximal end and a distal end; and a collapsible filter adjacent the distal end of the delivery member, the filter comprising a tube formed by braided filaments that define pores, the filter having at least one inlet opening that is substantially larger than the pores, the filter having an axis and tapered ends, wherein relative movement of the ends along the axis accompanies transformation of the filter between a collapsed configuration and a deployed configuration, and wherein the pore-defining filaments of the braided tube form a maximum included angle of about 90 degrees, as measured across the axis when the filter is in the deployed configuration.

7. The distal protection device of claim 6 further comprising:

a sheath being slidingly moveable over at least part of the filter for transforming the filter between the deployed configuration and the collapsed configuration.

8. The distal protection device of claim 6 wherein the deployed configuration is sized to fill a selected cross-sectional area distal to the treatment site.

9. The distal protection device of claim 6 wherein at least one of the braid filaments is a wire comprising radiopaque metal.

10. A system for treating a vascular stenosis, comprising:

an elongate delivery member having proximal and distal ends;

a collapsible filter mounted adjacent the distal end of the delivery member, the filter having a tube formed by braided filaments that define pores, the filter having at least one inlet opening that is substantially larger than the pores, the filter having an axis and tapered ends, wherein relative movement of the ends along the axis accompanies a transformation of the filter between a collapsed configuration and a deployed configuration, and wherein the pore-defining filaments of the braided tube form a maximum included angle of about 90 degrees, as measured across the axis when the filter is in the deployed configuration; and a vascular treatment catheter capable of being slidably disposed about the delivery member.

11. A system according to claim 10 further comprising a sheath capable of being slidably disposed about the delivery member and extendable over at least a proximal portion of the filter when the filter is in the collapsed configuration.

12. A system according to claim 10, wherein the vascular treatment catheter is a balloon angioplasty catheter.

13. A system according to claim 10, wherein the vascular treatment catheter is a stent delivery catheter.

14. A method of making a collapsible blood filter, the method comprising:

braiding wire-like filaments to form a tubular filter having pores therein, the filter having an axis, a deployed diameter and two ends, the filaments intersecting at a maximum angle of about 90 degrees, as measured across the axis when the filter is at the deployed diameter;

forming tapered ends on the filter by drawing the ends to a second diameter that is significantly smaller than the deployed diameter; and heat treating the filter to fix a selected shape thereof.

15. The method of making a blood filter according to claim 14, further comprising:

forming at least one inlet opening in a tapered end of the filter, the opening having a selected size and shape that is substantially larger than the pores by forcing a mandrel of the selected size and shape into a pore formed by the braided filaments.

16. The method of making a blood filter according to claim 14, wherein the braiding step further includes braiding a distal portion of the filter body more tightly than the remainder of the body.

17. The method of making a blood filter according to claim 14, wherein the wire-like filaments comprise shape-memory metal wires.

18. The method of making a blood filter according to claim 14, wherein at least one of the wire-like filaments is a wire comprising radiopaque metal.

* * * * *